US00PP37531P2

(12) United States Plant Patent
Marczynski

(10) Patent No.: US PP37,531 P2
(45) Date of Patent: Jul. 21, 2026

(54) ***CLEMATIS* PLANT NAMED 'Mystic River'**

(50) Latin Name: *Clematis integrifolia*
Varietal Denomination: Mystic River

(71) Applicant: Spring Meadow Nursery Inc, Grand Haven, MI (US)

(72) Inventor: Szczepan Marczynski, Pruszkow (PL)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,957

(22) Filed: Oct. 28, 2025

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02
See application file for complete search history.

*Primary Examiner* — Kent L Bell

(57) ABSTRACT

A new and distinct cultivar of *Clematis* plant named 'Mystic River' is disclosed, characterized by light blue tepals with a darker, violet-blue band. Tepals exhibit a unique longitudinal twisting/corkscrewing habit. Plants are vigorous, floriferous, and excellent container and landscape performers. The new cultivar is a *Clematis*, typically produced as an outdoor ornamental plant.

2 Drawing Sheets

Figure 1:
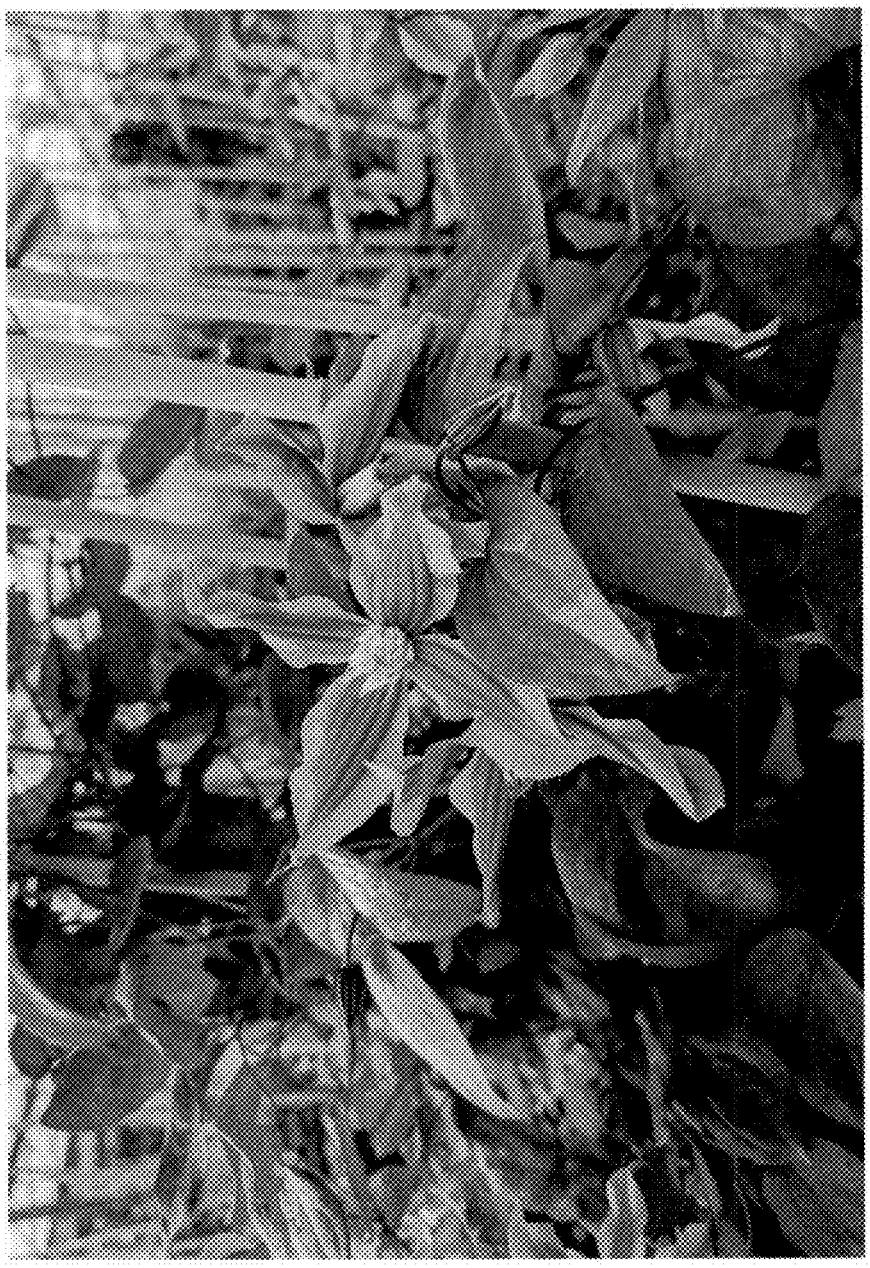

Latin name of the genus and species: *Clematis integrifolia.*

Cultivar denomination: 'MYSTIC RIVER'.

BACKGROUND OF THE INVENTION

The new cultivar is the product of a planned breeding program by the inventor to produce new *Clematis* cultivars with unique flower forms with possible suitability for amateur cut flowers; vigor, floriferousness, and health. 'Mystic River' is the result of the crossing of the seed parent, *Clematis* 'Kryspina', unpatented, and the pollen parent, *Clematis* 'Olgae', unpatented. The crossing was made in June 2015 at a nursery in Pruszków, Poland. 'Mystic River' was found and selected at the same location by the inventor in September 2018.

The first asexual reproduction was performed in April 2019 by softwood cuttings at the same nursery in Pruszków, Poland. *Clematis integrifolia* 'Mystic River' has been found to retain its distinctive characteristics through successive asexual propagations.

SUMMARY OF THE INVENTION

The cultivar 'Mystic River' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Mystic River' These characteristics in combination distinguish 'Mystic River' as a new and distinct *Clematis* cultivar:

1. Light blue tepals which exhibit a darker, violet-blue band.
2. Tepals which exhibit a unique, longitudinal twisting/corkscrewing habit.
3. Excellent vigor and floriferousness.

4. Excellent container and landscape performance.

PARENT COMPARISONS

Plants of the new cultivar 'Mystic River' are comparable to the seed parent in most horticultural characteristics; however, the new cultivar 'Mystic River' differs in the following:

1. Tepal color of the new cultivar is a light blue with a darker, violet-blue band, while the tepal color of the seed parent is magenta throughout.
2. Tepal shape of the new cultivar is narrowly elliptic, while the tepal shape of the seed parent is broadly elliptic to obovate.

Plants of the new cultivar 'Mystic River' are comparable to the pollen parent in most horticultural characteristics; however, the new cultivar 'Mystic River' differs in the following:

1. Flowers of the new cultivar are outward-facing, while flowers of the pollen parent are nodding/drooping.

COMMERCIAL COMPARISONS

Plants of the new cultivar 'Mystic River' are comparable to the commercial cultivar *Clematis* 'Cleminov51', unpatented. The two *Clematis* cultivars are similar in most horticultural characteristics; however, the new cultivar 'Mystic River' differs in the following:

1. Tepals of the new cultivar consistently exhibit a moderate to strong longitudinal twisting/corkscrewing habit. Tepals of this comparator occasionally exhibit a slight longitudinal twisting.
2. Tepal color of the new cultivar is lighter than the tepal color of this comparator.
3. Tepal color of the new cultivar exhibits a darker, central "bar", while the tepal color of this comparator is uniform throughout.

Plants of the new cultivar 'Mystic River' are comparable to the commercial cultivar *Clematis* 'Arabella', unpatented. The two *Clematis* cultivars are similar in most horticultural characteristics; however, the new cultivar 'Mystic River' differs in the following:

1. Tepals of the new cultivar consistently exhibit a moderate to strong longitudinal twisting/corkscrewing habit. Tepals of this comparator do not exhibit any longitudinal twisting.
2. Tepal color of the new cultivar exhibits a darker, central "bar", while the tepal color of this comparator is uniform throughout.

BRIEF DESCRIPTION OF THE PHOTOGRAPHS

The accompanying photograph in FIG. 1 illustrates in full color a typical plant of 'Mystic River' grown in a poly-greenhouse in Grand Haven, Michigan. This plant is approximately 2-3 years old, grown in a 3-gallon container.

Figure 2:
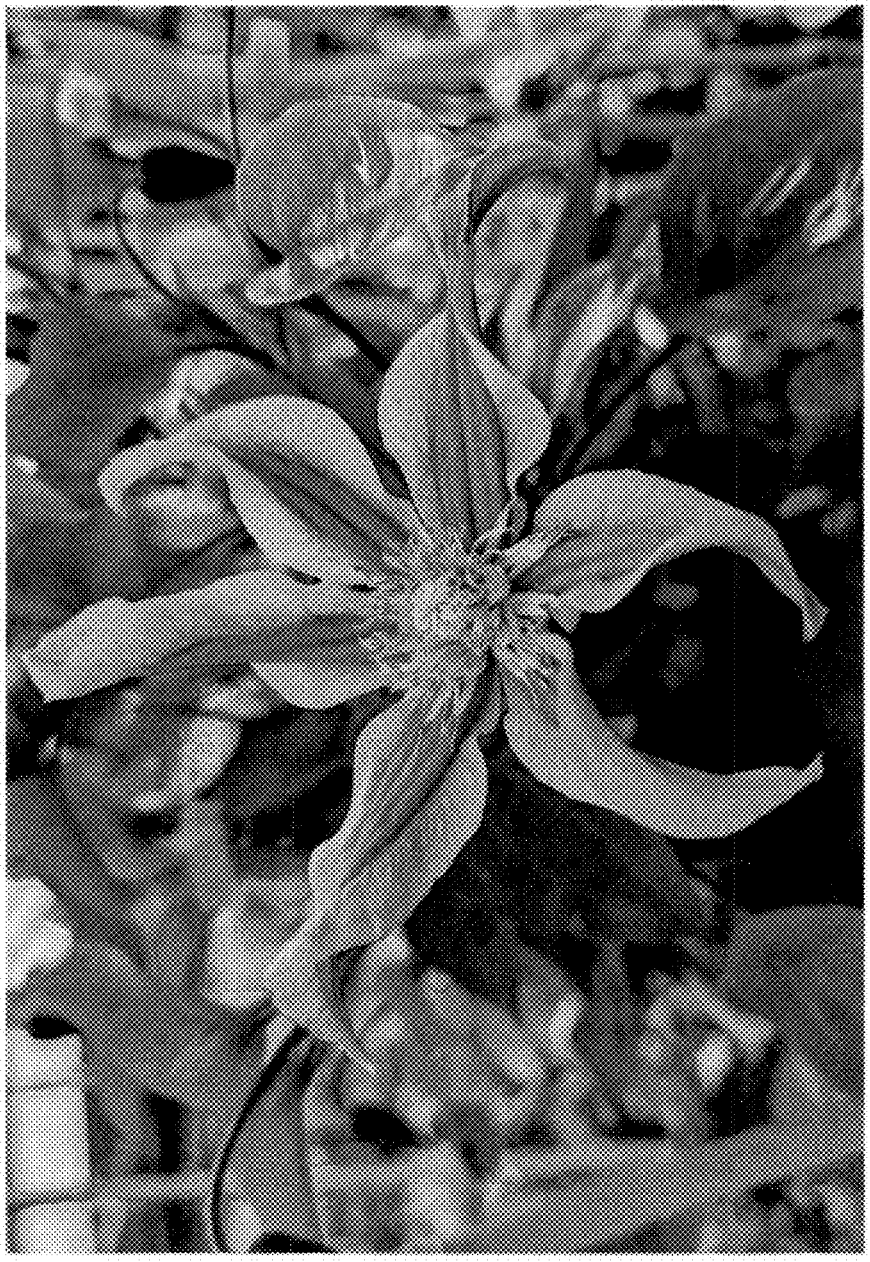

FIG. 2 illustrates in full color a close up of a flower of 'Mystic River'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'Mystic River' plants grown in a poly-greenhouse in Grand Haven, Michigan. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Clematis integrifolia* 'MYSTIC RIVER'.

PROPAGATION

Type of propagation typically used: Softwood cuttings.
Time to initiate roots: Approximately 6 weeks.
Time to produce a rooted cutting: 75 to 90 days.
Root description: Moderately dense, moderate to freely branching, medium thickness, fibrous. Tan in color, not accurately measured with R.H.S. chart.

PLANT

Age of plant described: 2 to 3 years.
Plant type: Perennial flowering vine.
Growth habit: Upwards and outwards in a vining, climbing, or sprawling manner.
Growth rate: High.
Vigor: High.
Plant spread: 130 cm.
Plant height: 70 cm.
Stem:
- *Branching habit.*—Freely branching.
- *Number of lateral branches.*—About 25.
- *Shape.*—Rounded.
- *Color.*—New Growth: RHS Yellow-Green 144A. Old Growth (Bark): RHS Greyed-Orange 176A and 166A.
- *Length.*—130 cm.
- *Width.*—3 mm.
- *Aspect.*—0° to 90° relative to the ground, depending upon staking/trellising.
- *Strength.*—Moderate to high.
- *Pubescence.*—Slight, on new growth only.
- *Internode Length.*—9 cm.

FOLIAGE

Leaf:
- *Arrangement.*—Opposite single and compound trifoliate.
- *Leaflet number.*—3 per leaf.
- *Length.*—Terminal Leaflet: 6 cm. Lateral Leaflet: 5.5 cm. Compound Leaf: 15 cm. Single Leaf: 6.5 cm.
- *Width.*—Terminal Leaflet: 3.25 cm. Lateral Leaflet: 3.25 cm. Compound Leaf: 10 cm. Single Leaf: 4.5 cm.
- *Leaflet shape.*—Narrowly ovate.
- *Leaflet apex.*—Acute.
- *Base.*—Terminal Leaflet: Obtuse. Lateral Leaflet: Oblique. Single Leaf: Oblique.
- *Margin.*—Terminal Leaflet: Entire. Lateral Leaflet: Entire. Single Leaf: Entire.
- *Leaflet texture.*—Upper Side: Glabrous. Under Side: Glabrous.
- *Color.*—Young foliage, upper side: Between RHS Green NN137B and Yellow-Green 146A. Young foliage, under side: Between RHS Green NN137B and Yellow-Green 146A. Mature foliage, upper side: RHS Yellow-Green 147A. Mature foliage, under side: Near RHS Green NN137C.
- *Pubescence.*—None.
- *Venation pattern.*—Palmate.
- *Venation color.*—Upper Side: Between RHS Green NN137B and Yellow-Green 146A. Under Side: Between RHS NN137B and Yellow-Green 146A.

Petiolule:
- *Length.*—Terminal Leaflet: 4 cm. Lateral Leaflet: 5 mm.
- *Width.*—Terminal Leaflet: 1 mm. Lateral Leaflet: 1 mm.
- *Color.*—Upper Side: RHS Yellow-Green 144A. Under Side: RHS Yellow-Green 144A.
- *Texture.*—Glabrous, both sides.

Petiole:
- *Length.*—Terminal Leaflet: 4 cm. Lateral Leaflet: 5 mm.
- *Width.*—Terminal Leaflet: 1 mm. Lateral Leaflet: 1 mm.
- *Color.*—Upper Side: RHS Yellow-Green 144A. Under Side: RHS Yellow-Green 144A.
- *Texture.*—Glabrous, both sides.

FLOWER

Natural flowering season: Summer (May-June) with lesser repeat flowering into the early fall.
Flower arrangement: Single rotate flowers which emerge from the leaf axils along the lengths of lateral branches, but primarily at the apices.
Flower form: Rotate.

Flowering habit: Freely flowering with abundant blooms in summer (May-June) with lesser repeat flowering into the early fall.
Flowers per lateral stem: 3 to 5.
Buds per lateral stem: 1 to 2.
Flowers and buds per plant: 100 to 175.
Fragrance: None.
Buds:
*Length.*—2 cm.
*Diameter.*—1 cm.
*Shape.*—Narrowly ovate.
*Color.*—RHS Violet-Blue N92D.
Flower:
*Shape.*—Whorl.
*Length.*—10 cm.
*Diameter.*—10 cm.
*Depth.*—3 cm.
*Aspect.*—Outward, slightly drooping.
*Longevity.*—2 weeks on plant.
*Persistence.*—Self-cleaning.
Tepals:
*Appearance.*—Light blue tepals with a darker, violet-blue band; Tepals exhibit a longitudinal twisting/corkscrewing quality; Margins are moderately ruffled.
*Arrangement.*—Rotate.
*Quantity.*—5 to 6.
*Apex.*—Acuminate.
*Base.*—Truncate.
*Fused.*—No.
*Shape.*—Narrowly elliptic.
*Margin.*—Entire with a moderate ruffling/undulating quality.
*Length.*—5.5 cm.
*Width.*—2.75 cm.
*Texture.*—Glabrous and silky, both sides.
*Color.*—When opening, upper side: RHS Violet-Blue 90C with a Violet Blue 90A bar. When opening, under side: RHS Violet-Blue 90C with a Violet Blue 90A bar. Fully opened, upper side: RHS Violet-Blue 92B with a Violet-Blue 92A bar. Fully opened, under side: RHS Violet-Blue 92B with a Violet-Blue 92A bar. Fading, upper side: RHS Violet-Blue 97B with a Violet-Blue 97A bar. Fading, under side: RHS Violet-Blue 97B with a Violet-Blue 97A bar.
Peduncle:
*Length.*—8 cm.
*Diameter.*—2 mm.
*Angle.*—0 to 45° from vertical.
*Strength.*—Moderate.
*Texture.*—Lightly pubescent.
*Color.*—RHS Yellow-Green 146A.

REPRODUCTIVE ORGANS

Stamens:
*Number.*—About 80.
*Filament length.*—1 cm.
*Filament color.*—RHS White NN155B.
Anther:
*Length.*—0.5 cm.
*Shape.*—Linear.
*Color.*—RHS Yellow 8C.
*Pollen.*—Moderate to high.
*Pollen color.*—RHS Yellow 8C.
Pistil:
*Number.*—About 80.
*Length.*—1 cm.
Stigma:
*Shape.*—Filamentous.
*Color.*—RHS Green-Yellow 157C.
*Style length.*—0.5 cm.
*Style color.*—RHS Green-Yellow 157C.

OTHER CHARACTERISTICS

Fruit and Seed: Not observed.
Disease and pest resistance: Resistance or susceptibility to diseases or pests of *Clematis* not observed to date.
Temperature range: Tolerant to USDA zones 4 to 11.

What is claimed is:

1. A new and distinct cultivar of *Clematis* plant named 'Mystic River' as herein illustrated and described.

* * * * *